United States Patent [19]
Wijkamp et al.

[11] Patent Number: 5,766,206
[45] Date of Patent: Jun. 16, 1998

[54] METHOD AND DEVICE FOR HEMOSTATIC TREATMENT FOLLOWING CATHETERIZATION

[75] Inventors: Arnoldus Cornelius Johannes Maria Wijkamp, Roden, Netherlands; Yvo Madeleine Albert Taeymans, DePinte, Belgium

[73] Assignee: Cordis Corporation, Miami Lakes, Fla.

[21] Appl. No.: 299,368

[22] Filed: Sep. 1, 1994

[30] Foreign Application Priority Data

Sep. 3, 1993 [EP] European Pat. Off. ........ 9301526

[51] Int. Cl.⁶ .................................................. A61B 17/04
[52] U.S. Cl. ........................... 606/213; 606/215; 604/15
[58] Field of Search .................... 606/213–216; 128/672, 673, 748; 604/118, 121, 11–18

[56] References Cited

U.S. PATENT DOCUMENTS

| | | | |
|---|---|---|---|
| 2,646,042 | 7/1953 | Hu | 604/118 |
| 4,744,364 | 5/1988 | Kensey | |
| 4,804,358 | 2/1989 | Karcher et al. | 604/118 |
| 4,832,688 | 5/1989 | Sagae et al. | 604/53 |
| 4,852,568 | 8/1989 | Kensey | |
| 4,890,612 | 1/1990 | Kensey | 606/213 |
| 5,021,059 | 6/1991 | Kensey et al. | 606/213 |
| 5,037,386 | 8/1991 | Marcus et al. | 604/118 |
| 5,061,274 | 10/1991 | Kensey | 606/213 |
| 5,108,421 | 4/1992 | Fowler | 606/213 |
| 5,123,329 | 6/1992 | Irwin | 89/161 |
| 5,129,882 | 7/1992 | Weldon et al. | 604/96 |
| 5,176,629 | 1/1993 | Kullas | 604/118 |
| 5,192,300 | 3/1993 | Fowler | 606/213 |
| 5,221,259 | 6/1993 | Weldon et al. | 604/96 |
| 5,222,974 | 6/1993 | Kensey et al. | 606/15 |
| 5,275,616 | 1/1994 | Fowler | 606/213 |
| 5,282,827 | 2/1994 | Kensey et al. | 606/215 |

FOREIGN PATENT DOCUMENTS

| | | | |
|---|---|---|---|
| 2087906 | 7/1993 | Canada . | |
| 0482350 | 4/1992 | European Pat. Off. . | |
| 534646 | 3/1993 | European Pat. Off. | 606/213 |

Primary Examiner—Gary Jackson
Attorney, Agent, or Firm—Thomas R. Vigil; Henry W. Collins; Michael W. Montgomery

[57] ABSTRACT

The device for hemostatic treatment of a puncture opening following catheterization comprises an elongate tubular penetration member having a longitudinal axis, an internal end, an external end and a passageway therein including at least one longitudinal channel which extends at least a major portion of the distance between the internal and external ends. A pressure gauge is connected by connecting structure to the external end of the penetration member and to the longitudinal channel. A reservoir for hemostatic pharmacon is provided and is connected to the external end of the penetration member. The penetration member is provided with an opening, close to the internal end of the penetration member, for communicating the pressure gauge to the puncture opening.

5 Claims, 3 Drawing Sheets

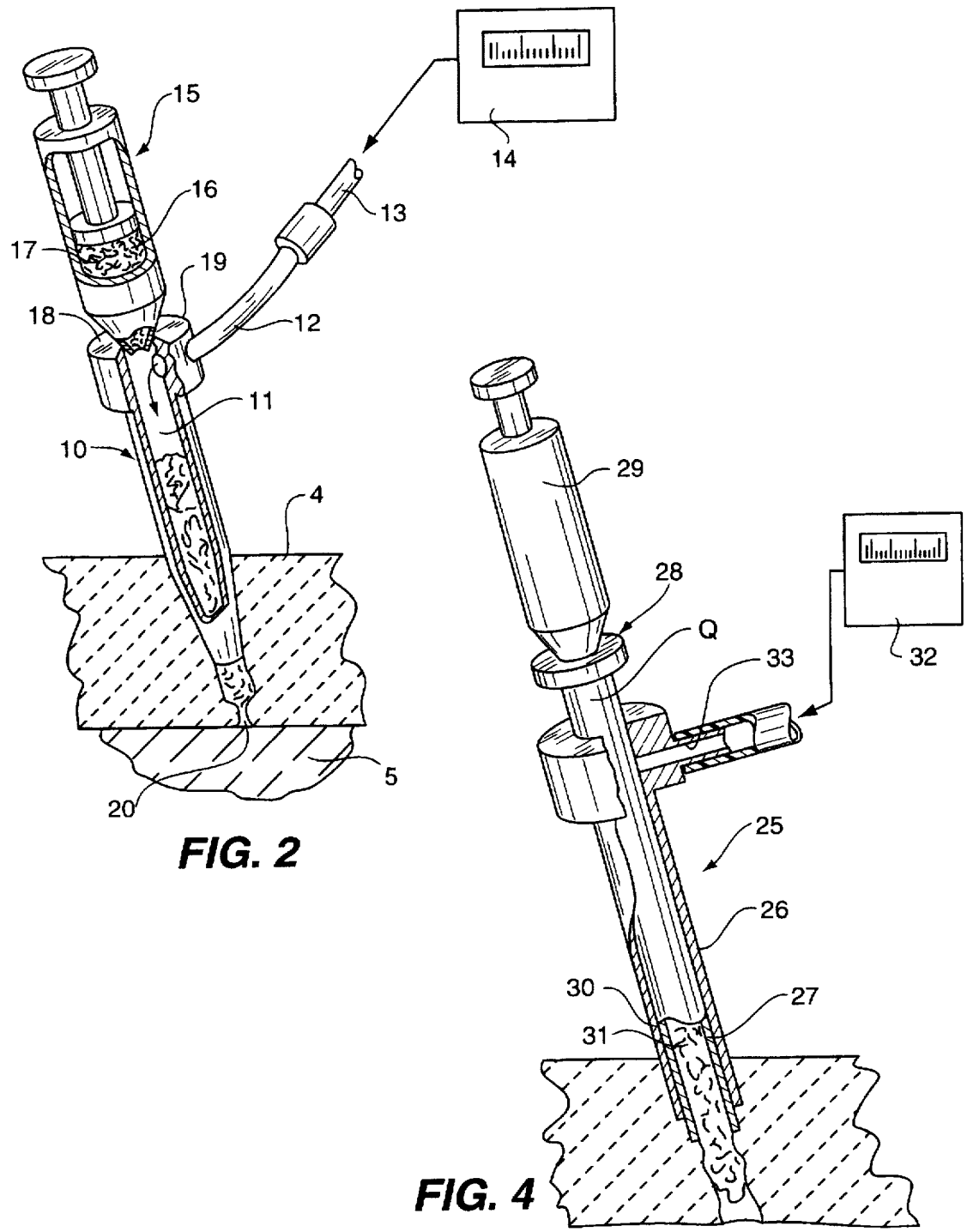

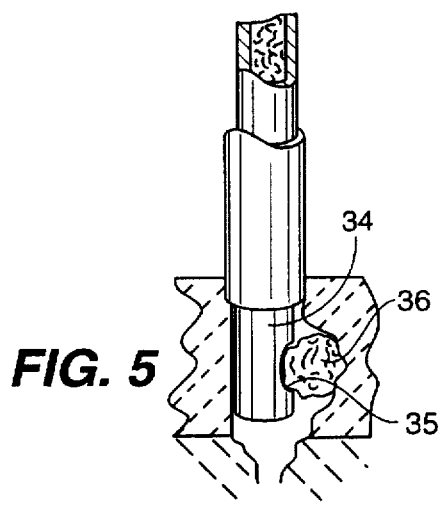
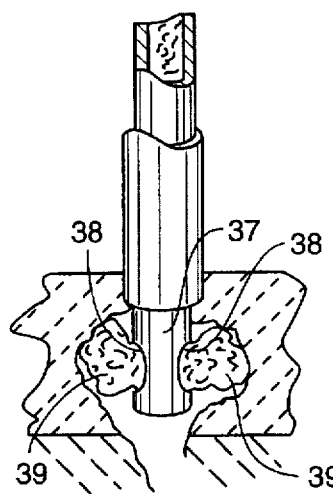
FIG. 5
FIG. 6
FIG. 7
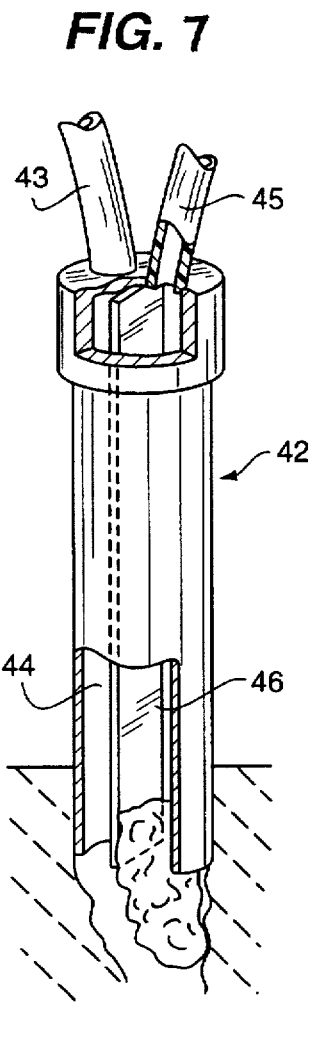
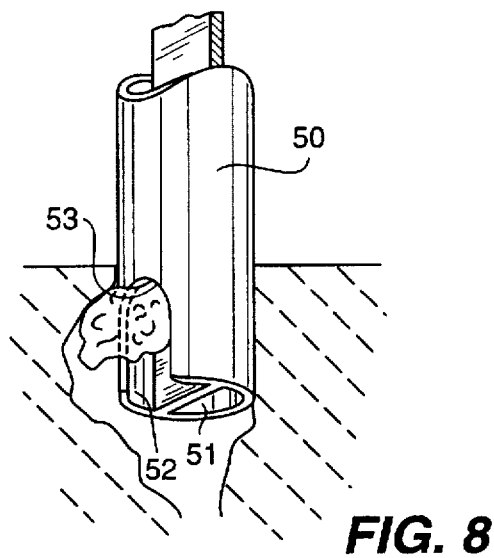
FIG. 8
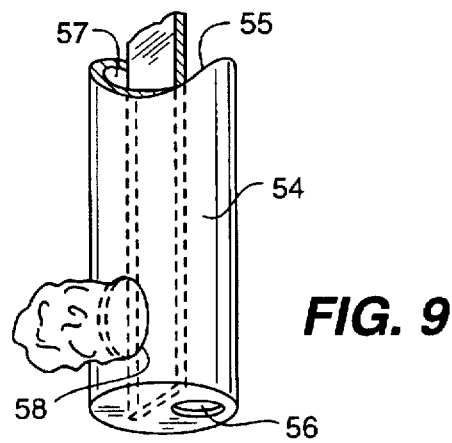
FIG. 9

METHOD AND DEVICE FOR HEMOSTATIC TREATMENT FOLLOWING CATHETERIZATION

BACKGROUND OF THE INVENTION

1. Field of the Invention

The present invention relates to a device used to carry out hemostatic treatment following catheterization.

Following catheterization and after removal of a catheter introduction member inserted through the skin and the vascular wall, a puncture wound will remain which is at times difficult to close and may continue to bleed for a long time. The device of the present invention simplifies this procedure.

2. Description of the Related Art Including Information Disclosed Under 37 CFR §§ 1.97–1.99

Heretofore, it has been a well known procedure to apply a plug of hemostatic pharmacon up against the vascular wall adjacent a puncture wound to stem the flow of blood. However it is difficult to correctly position the collagen plug.

Examples of previously proposed methods and devices for sealing a puncture wound are disclosed in the following U.S. patents and foreign patent publications:

| U.S. Pat. No. | Patentee |
| --- | --- |
| 5,282,827 | Kensey et al. |
| 5,275,616 | Fowler |
| 5,222,974 | Kensey et al. |
| 5,221,259 | Weldon |
| 5,192,300 | Fowler |
| 5,129,882 | Weldon |
| 5,123,329 | Weldon |
| 5,108,421 | Fowler |
| 5,061,274 | Kensey |
| 5,021,059 | Kensey et al. |
| 4,890,612 | Kensey |
| 4,852,568 | Kensey |
| 4,832,688 | Sagae et al. |
| 4,744,364 | Kensey |

Canadian Patent No. 2,087,906 assigned to C. R. Bard, Inc.
EP Published Patent Application No. 0 482 350 assigned to Datascope Investment Corp.

The Sagae et al. U.S. Pat. No. 4,832,688 discloses a specific catheter embodiment for repairing a hole in a blood vessel wall. The catheter comprises at least one balloon which is inflated in an area to the opening of a wall in a vessel so as to block the blood flow. Subsequently, a collagen plug is deposited at the place of the opening, and this collagen plug is subsequently pushed and pressed against the vessel wall by means of the balloon. A pressure gauge is provided for monitoring the pressure inside the balloon so that it is inflated properly.

The Kensey et al. U.S. Pat. Nos. 5,282,827 and 5,222,974 are concerned with the problem of closing a puncture in a vessel wall and teach closing of the puncture by introducing a closing element into the vessel and pulling it tight against the inside of the wall. Thereafter, some hemostatic pharmacon is introduced into the puncture. The closure element prevents flow of the pharmacon into the blood vessel.

EP Published Application No. 0 482 350 discloses a method for displaying a plug a specific way at the outside of a puncture in a vessel wall.

As will be described in greater detail hereinafter, the method and device of the present invention differ from the teachings of the prior art patent publications listed above by providing for the monitoring of pressure in the puncture opening to properly place a plug of hemostatic pharmacon in the puncture opening while slowly withdrawing a penetration member through the opening.

SUMMARY OF THE INVENTION

According to the present invention there is provided a device for hemostatic treatment of a puncture opening following catheterization. The device comprises an elongate tubular penetration member having a longitudinal axis, an internal end, an external end and a passageway therein including at least one longitudinal channel which extends at least a major portion of the distance between the internal and external ends. A pressure gauge is connected by connecting structure to the external end of the penetration member and to the longitudinal channel. A reservoir for hemostatic pharmacon is provided and is connected to the external end of the penetration member. The penetration member is provided with an opening, close to the internal end of the penetration member, for communicating the pressure gauge to the puncture opening.

Following catheterization, the penetration member which has first been inserted through a puncture opening through the skin and the vascular wall, is withdrawn gradually while observing the pressure gauge connected to the penetration member. When the pressure gauge indicates a falling pressure, it is an indication that the end of the penetration member has been drawn back to a position right inside or just outside the vascular wall. By way of the reservoir, which is connected to the longitudinal channel of the penetration member, a hemostatic pharmacon is deposited in exactly the right position. Thus, it is ensured that the hemostatic pharmacon will not end up in the blood vessel itself which could result in a serious complication for the patient.

As the phase during which the hemostatic pharmacon is supplied follows the phase of pressure measurement, one and the same channel can be used for both the pressure measurement and the supply of the hemostatic pharmacon.

More exact positioning of the penetration member and, in particular, of the opening through which the hemostatic pharmacon will be ejected in or close to the vascular wall can be effected by measuring pressure downstream of an opening of a hemostatic pharmacon delivery channel in the penetration member. Then the hemostatic pharmacon will always be ejected in a position a little further back from where the pressure is measured so that one can be assured that this hemostatic pharmacon will be deposited in the right place.

Also according to the present invention there is provided a method for carrying out a hemostatic treatment of a puncture opening subsequent to the performance of a catheterization procedure in which a catheter had been inserted into and withdrawn from a vessel through a penetration member which had been inserted through the puncture opening and through the vascular wall of the vessel and which has passage means therein including at least one longitudinal channel. The method comprises the steps of:

coupling a pressure gauge to an outer end of the longitudinal channel;

sensing pressure at the inner end of the longitudinal channel while simultaneously slowly withdrawing the penetration member;

noting when there is a pressure drop indicating that the inner end of the longitudinal channel has been withdrawn from the vessel and is located within the tissue surrounding the puncture opening;

introducing through the penetration member hemostatic pharmacon for plugging the puncture opening; and

3 withdrawing the penetration member from the puncture opening.

BRIEF DESCRIPTION OF THE DRAWINGS

FIG. 2 shows more or less schematically a device constructed according to the teachings of the present invention in a position of use.

FIG. 4 illustrates another embodiment of a device constructed according to the teachings of the present invention.

FIGS. 5 and 6 show sections of two other embodiments of a device constructed according to the teachings of the present invention.

FIGS. 7, 8 and 9 show schematically three further embodiments of devices constructed according to the teachings of the present invention.

DESCRIPTION OF THE PREFERRED EMBODIMENT(S)

Figure 1:
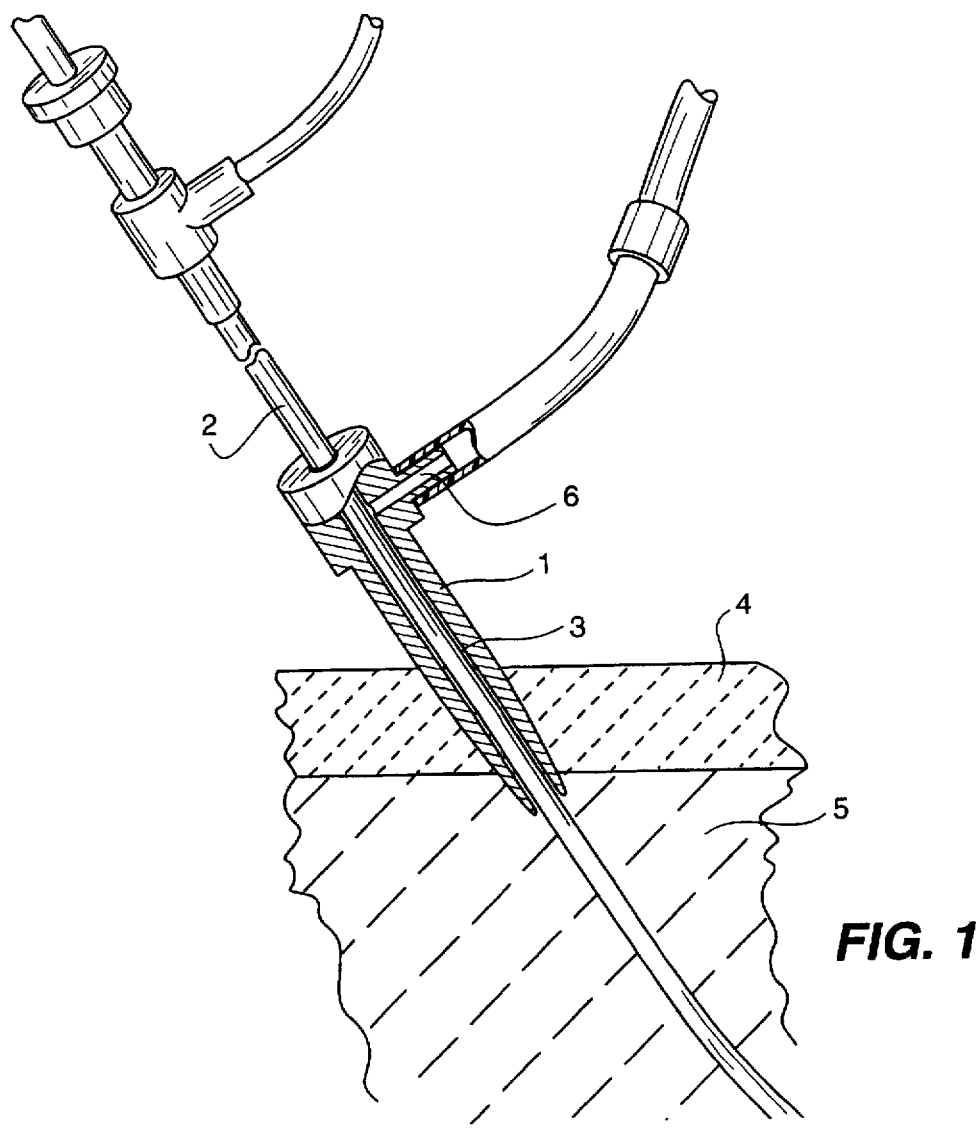
FIG. 1 shows schematically an introduction or penetration member for an angiographic catheter in the position of use.

FIG. 1 illustrates an introduction or penetration member 1 which is introduced by means of known appliances, not shown in FIG. 1, through a puncture opening in the skin and the wall 4 of a blood vessel. The introduction member 1 has a passageway comprising at least one longitudinal channel 3 through which a catheter 2 can be introduced which consequently will end up in the lumen 5 of the blood vessel and which can be advanced via the blood vessel to the desired, to be treated or to be investigated area.

The introduction member is of a known type and is, in this case, fitted with a side connection 6, connected with the longitudinal channel 3.

FIG. 2 shows a device constructed according to the present invention. The device comprises a penetration member 10, which can, for instance, be an introduction member such as the introduction member shown in FIG. 1. The penetration member 10 has a passageway therein comprising at least one longitudinal channel 11 which, close to an external end of the member 10 remains outside the body of the patient and ends in a connecting piece 12. The connecting piece 12 is, with the aid of connecting structure 13, in this example of the embodiment made of a tube, connected with a pressure gauge 14 which consequently can indicate the pressure in the channel 11.

The device according to the invention comprises furthermore supply structure 15 for a hemostatic pharmacon, which supply structure 15 comprises a reservoir 17 for the hemostatic pharmacon 16. The supply structure 15 has been made in the form of a hypodermic syringe and is fitted at its outlet with a connecting member 18 which is associated with a connecting member 19 at the external end of the penetration member 10. This connecting member 19 is connected to a longitudinal channel which in this case is the same longitudinal channel 11 to which the connecting piece 12 is connected.

The device can be used in the following manner.

Following catheterization and after removal of the catheter, the penetration member 10 is introduced through the vascular wall 4. In case the introduction member already used for introducing the catheter is used as a penetration member, it obviously will not be necessary to introduce it

4 once again. With the aid of the connecting structure 13, the pressure gauge 14 is connected to the connecting piece 12. In the situation wherein the penetration member 10 extends into the lumen 5 of the blood vessel, the pressure gauge will indicate the pressure prevailing in the lumen 5 of the blood vessel 4. When the penetration member 10 is withdrawn slowly, the pressure indicated by the pressure gauge 14 will fall away gradually as soon as the internal end of the penetration member is withdrawn from the lumen 5 of the blood vessel.

Figure 3:
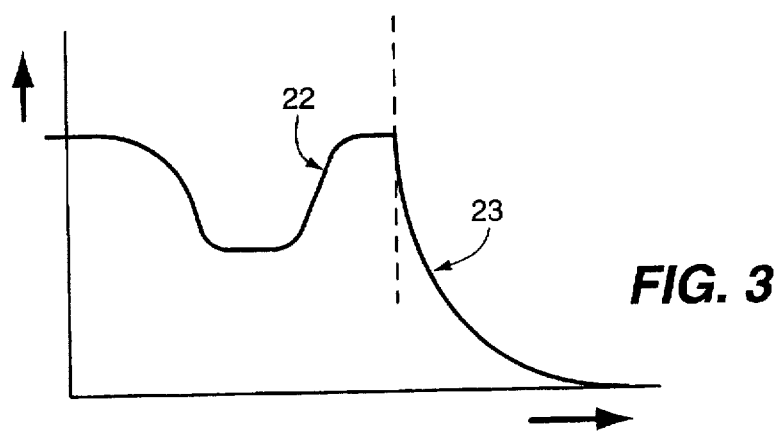
FIG. 3 represents a graph of an example of the pressure changes as measured during the practice of the method using the device shown in FIG. 2.

This is illustrated schematically in the graph of FIG. 3. This graph indicates time on the horizontal axis and pressure on the vertical axis. As long as the penetration member extends into the lumen 5 of the blood vessel, a pressure measurement indicated at 22 is obtained from inside the lumen of the blood vessel. On withdrawal, the internal end of the penetration member will pass the opening 20 in the wall 4 of the blood vessel. This opening 20 will contract slightly due to which the pressure measurement will fall off as indicated in FIG. 3 at 23. As soon as the penetration member has been withdrawn sufficiently, which can be read on the pressure gauge 14, the supply structure 15 will be activated and the hemostatic pharmacon 16 will be ejected through the longitudinal channel 11, thus closing the puncture wound.

It should be noted that in the drawings the vascular wall 4 has been drawn relatively thick. For a clear understanding of the invention, one can, however, look upon it as being the vascular wall itself together with the adjoining layers of tissue. The hemostatic pharmacon does not need to be conveyed to inside the wall of the blood vessel itself but can be conveyed to the adjoining layers of tissue.

The device 25 shown in FIG. 4 has been made slightly different than the device shown in FIG. 2. An insertion piece 27 is inserted into the penetration member 26 when, with the aid of the pressure gauge 32, it has been established that the penetration member has been withdrawn sufficiently far. The pressure gauge 32 is, by way of schematically indicated connecting structure, connected to the connecting piece 33 which is connected directly to the central longitudinal channel 30 of the penetration member 26. The insertion piece 27 has a tubular shape and comprises its own longitudinal channel 31 which ends, close to the external end, in a connecting member situated inside the connecting means 28 by way of which a supply structure 29 is connected to the insertion piece 27.

FIG. 5 shows the bottommost or internal end of a device 25 of the type as shown in FIG. 4 with a differently shaped insertion piece. In FIG. 5 the insertion piece 34 comprises a side hole 35, so that the hemostatic pharmacon 36 is ejected sideways. Thus, the risk that the hemostatic pharmacon will enter the blood vessel itself via the opening in the vascular wall, which could entail serious complications for the patient, is minimized.

FIG. 6 shows a variation of the device wherein the insertion piece 37 has a number of side holes 38 for the purpose of ejecting the hemostatic pharmacon 39 sideways around the entire circumference.

In the case of the penetration member 42, as shown in FIG. 7, the connection member 45 and the connection piece 43 are connected to separate channels 46 and 44, respectively, inside the penetration member 42. Because of this, pressure measurement with the aid of the pressure gauge connected with the connecting piece 43 can continue, while the hemostatic pharmacon is ejected via the connection member 45 and the longitudinal channel 46. The pressure measurement can thus give an indication as to the progress of the supply of the hemostatic pharmacon.

In FIG. 8 a somewhat altered embodiment is shown. In this case, the penetration member 50 also comprises separate channels 51 and 52 connected with the connecting piece and the connecting member, respectively. The internal end 53 of the channel 52 ends at some distance before the internal end of the channel 51. Consequently, the hemostatic pharmacon is always ejected at a somewhat greater distance from the opening in the vascular wall, so that careful positioning is possible. The penetration member 50 only needs to be withdrawn to the point where the pressure gauge indicates a reduction in pressure. This is an indication of passing the puncture in the vascular wall. When subsequently the supply structure is activated, the hemostatic pharmacon will be deposited in the right place.

FIG. 9 shows an embodiment developed to an even greater degree. The penetration member 54 is essentially closed off at its bottommost or internal end. The channel 55 connected with the connecting piece, ends in an opening 56 at the bottom of the penetration member 54. The channel 57 connected to the connecting member ends in a side hole 58.

We claim:

1. A method for carrying out a hemostatic treatment of a puncture opening subsequent to the performance of a catheterization procedure in which a catheter had been inserted into and withdrawn from a vessel through a penetration member which had been inserted through the puncture opening and through the vascular wall of the vessel and which has passage means therein including at least one longitudinal channel, said method comprising the steps of:

coupling a pressure gauge to an outer end of the at least one longitudinal channel;

monitoring pressure at an inner end of the at least one longitudinal channel while simultaneously slowly withdrawing the penetration member;

noting when there is a pressure drop indicating that the inner end of the at least one longitudinal channel has been withdrawn from the vessel and is located within the tissue surrounding the puncture opening;

introducing through the penetration member hemostatic pharmacon for plugging the puncture opening;

withdrawing the penetration member from the puncture opening; and, sensing the pressure in an opening, defining the inner end of the at least one longitudinal channel, in a side wall of the penetration member at a point upstream from an inner end of the penetration member.

2. The method of claim 1 including the step of:

delivering the hemostatic pharmacon at a point upstream of the inner end of the penetration member.

3. A method for carrying out a hemostatic treatment of a puncture opening subsequent to the performance of a catheterization procedure in which a catheter had been inserted into and withdrawn from a vessel through a penetration member which had been inserted through the puncture opening and through the vascular wall of the vessel and which has passage means therein including at least one longitudinal channel, said method comprising the steps of:

coupling a pressure gauge to an outer end of the at least one longitudinal channel;

monitoring pressure at an inner end of the at least one longitudinal channel while simultaneously slowly withdrawing the penetration member;

noting when there is a pressure drop indicating that the inner end of the longitudinal channel has been withdrawn from the vessel and is located within the tissue surrounding the puncture opening;

introducing through the penetration member hemostatic pharmacon for plugging the puncture opening;

withdrawing the penetration member from the puncture opening; and, supplying the hemostatic pharmacon at a position upstream from the inner end of the penetration member.

4. The method of claim 3 including the steps of:

providing in the passage means a separate, second longitudinal channel and coupling same to supply means operable to supply hemostatic pharmacon to the second longitudinal channel whereby pressure is sensed through the at least one longitudinal channel at the inner end of the penetration member and pharmacon is supplied through the second longitudinal channel to the tissue surrounding the puncture opening at a position upstream from the inner end of the penetration member.

5. A device for hemostatic treatment of a puncture opening following catheterization, said device comprising an elongate tubular penetration member having a longitudinal axis, an internal end, an external end and passage means therein including at least one longitudinal channel which extends at least a major portion of the distance between said internal and external ends, a pressure gauge, first connecting means for connecting said pressure gauge to said external end supply means including a reservoir for hemostatic pharmacon, second connecting means for connecting said reservoir to said external end of said penetration member, and said penetration member having communicating means, close to said internal end of said penetration member, for communicating said pressure gauge to the puncture opening, said passage means comprising first and second separate longitudinal channels in said penetration member and said penetration member having a side opening therein upstream from said internal end and communicating with said second longitudinal channel.

* * * * *